(12) United States Patent
Roy et al.

(10) Patent No.: US 7,106,479 B2
(45) Date of Patent: Sep. 12, 2006

(54) SYSTEMS AND METHODS FOR ENHANCING THE VIEWING OF MEDICAL IMAGES

(75) Inventors: Stephen C. Roy, Boca Raton, FL (US); John D. Hodgeman, Boca Raton, FL (US)

(73) Assignee: Stryker Corporation, Kalamazoo, MI (US)

(*) Notice: Subject to any disclaimer, the term of this patent is extended or adjusted under 35 U.S.C. 154(b) by 814 days.

(21) Appl. No.: 09/975,027

(22) Filed: Oct. 10, 2001

(65) Prior Publication Data

US 2003/0069897 A1 Apr. 10, 2003

Related U.S. Application Data

(60) Provisional application No. 60/238,428, filed on Oct. 10, 2000.

(51) Int. Cl.
*G06F 7/00* (2006.01)
(52) U.S. Cl. .................. 358/3.27; 358/1.15; 382/128
(58) Field of Classification Search ............... 382/128, 382/131, 132; 358/1.15, 1.16, 1.17, 1.18, 358/402, 403, 450, 3.27
See application file for complete search history.

(56) References Cited

U.S. PATENT DOCUMENTS

| | | | |
|---|---|---|---|
| 4,764,870 A | 8/1988 | Haskin | |
| 4,817,050 A | 3/1989 | Komatsu et al. | |
| 4,910,609 A | 3/1990 | Nicholas et al. | |
| 5,179,651 A | 1/1993 | Taaffe et al. | |
| 5,272,625 A | 12/1993 | Nishihara et al. | |
| 5,291,401 A | 3/1994 | Robinson | |
| 5,321,520 A | 6/1994 | Inga et al. | |
| 5,360,446 A | * 11/1994 | Kennedy | 128/898 |
| 5,384,643 A | 1/1995 | Inga et al. | |
| 5,416,602 A | 5/1995 | Inga et al. | |
| 5,469,353 A | 11/1995 | Pinsky et al. | |
| 5,513,101 A | 4/1996 | Pinsky et al. | |
| 5,655,084 A | 8/1997 | Pinsky et al. | |
| 5,715,823 A | 2/1998 | Wood et al. | |
| 5,802,518 A | 9/1998 | Karaev et al. | |
| 5,810,747 A | 9/1998 | Brudny et al. | |

(Continued)

FOREIGN PATENT DOCUMENTS

DE 196 25 836 A1 6/1996

(Continued)

OTHER PUBLICATIONS eMed Technologies Advertisement, Stop hanging on to the old system. It's time to get your practice on the web.

(Continued)

*Primary Examiner*—Thomas D. Lee
(74) *Attorney, Agent, or Firm*—Snell & Wilmer L.L.P.

(57) ABSTRACT

The present invention provides systems and methods for enhancing the delivery and display of medical images over a network. Authorized users may access and view images by accessing a secure server and selecting images for viewing. Various characteristics of the image or images being viewed may be manipulated. Additionally, measuring devices, such as a goniometer, may be placed on an image to measure distances, angles and the like. In one embodiment, one or more templates, for example of medical devices, may be placed on an image and manipulated. In another embodiment, two or more users may view the same image simultaneously, while also viewing a template, measuring device, image manipulations and the like simultaneously. In yet another embodiment, two or more users may discuss one or more images via a discussion board.

22 Claims, 5 Drawing Sheets

U.S. PATENT DOCUMENTS

| | | | |
|---|---|---|---|
| 5,836,877 A | 11/1998 | Zavislan | |
| 5,851,186 A | 12/1998 | Wood et al. | |
| 5,857,967 A | 1/1999 | Frid et al. | |
| 5,949,491 A | 9/1999 | Callahan et al. | |
| 6,006,191 A | 12/1999 | DiRienzo | |
| 6,032,120 A | 2/2000 | Rock et al. | |
| 6,064,490 A | 5/2000 | Minamizawa | |
| 6,076,166 A * | 6/2000 | Moshfeghi et al. | 713/201 |
| 6,101,536 A | 8/2000 | Kotani et al. | |
| 6,157,675 A | 12/2000 | Mitsuhashi et al. | |
| 6,344,853 B1 * | 2/2002 | Knight | 345/629 |
| 6,424,996 B1 * | 7/2002 | Killcommons et al. | 709/206 |
| 2001/0011301 A1 | 8/2001 | Sato et al. | |
| 2001/0032246 A1 | 10/2001 | Fardella et al. | |

FOREIGN PATENT DOCUMENTS

| | | |
|---|---|---|
| DE | 196 25 839 A1 | 6/1996 |
| EP | 0 844 581 A2 | 5/1998 |
| EP | 0 844 781 A2 | 5/1998 |
| JP | 1128462 A | 3/1998 |
| JP | 2000066969 A | 3/2000 |
| JP | 2000224542 A | 8/2000 |
| WO | WO 99/64971 | 12/1999 |

OTHER PUBLICATIONS

Stentor Intelligent Informatics Advertisement, Stentor enterprise image management.
GE ASP Solutions Article, The Healthcare ASP, Apr. 2000.
R. Ernest Waaser, Demystifying ASP, Nov./Dec. 2000, Imaging Economics Supplement p. 3.
Rich Mancilla, ASP Infrastructure: Beyond Copper Wire and Fiber Optics, Nov./Dec. 2000, Imaging Economics Supplement pp. 4,5 & 19.
Nicole Pliner, Patricia Whelan and Keith J. Dreyer, Financially Speaking, Nov./Dec. 2000, Imaging Economics Supplement pp. 6-8.
Rich Smith, Q&A: Issues in ASP, Nov./Dec. 2000, Imaging Economics Supplement pp. 13-16.
Osman Ratis, Outsourcing the Electronic Medical Record, Nov./Dec. 2000, Imaging Economics Supplement pp. 9, 10 & 12.
Keith J. Dreyer, PACS on call, Nov./Dec. 2002 Imaginig Economics Supplement pp. 50, 52, 55 & 90.
Carter H. Yates, Next Generation PACS, Nov./Dec. 2000 Imaging Economics Supplement pp. 17-19.
George Wiley, Warning: Teleradioactive?, Nov./Dec. 2000 Imaging Economics pp. 24, 26, 28, 30 & 92.
BRIT Systems Advertisement, Connect to the Internet with eRadfiles and become wildly efficient!.
COMDISCO Advertisement, [I'm growing too fast] I'm Your Digital Information.
Paul E. Christian, Donald A. Baune, Frederick L. Datz; Clinical and Educational PACS, Teleradiology and Conferencing using Low-Cost Unix Workstations; http://wwwrad.med.utah.edu/nucmed/PACS.html.
http://www.amicas.com/index.html . . . , Amicas, Inc. Amicas Net, 5 pages, Apr. 26, 2000.
http://telemedtoday.com/ . . . Telemedicine Today Magazine, 22 pages., Apr. 26, 2000.
http://tims.com/ . . . Tims Teleradiology Home Page, 4 pgs., May 12, 2000.
http://informedcare.com/medvision/visitran.htm, MedVision, 2 pgs., May 12, 2000.
http://dataviewimaging.com/webradiology.htm, 2 pgs., May 12, 2000.
http://siriucorp.com/webserver.html, 2 pgs., May 12, 2000.
http://www.mediface.com/piwe_body.html, Mediface Co., Ltd., 1 pg., May 12, 2000.
http://inphact.com/info/body.htm, Inphact, 2 pgs., May 12, 2000.
http://www.kodak.com/US/en/corp/pressRelease/pr20000501-01.shtml, Eastman Kodak Company, 2 pgs., May 12, 2000.
Journal of Digital Imaging, vol. 7, No. 1, Feb. 1994; www.scarnet.org/JDIContents/JDIFeb94.html.

* cited by examiner

SYSTEMS AND METHODS FOR ENHANCING THE VIEWING OF MEDICAL IMAGES

RELATED APPLICATIONS

This application claims the benefit of, and priority to, U.S. Provisional Patent Application Ser. No. 60/238,428, filed Oct. 10, 2000, which is incorporated herein by reference in its entirety.

FIELD OF INVENTION

The present invention generally relates to systems and methods for enhancing the viewing of images. More particularly, the present invention relates to systems and methods for enhancing the remote viewing of medical images stored on a secure server via a network.

BACKGROUND OF THE INVENTION

Medical images, such as conventional radiographs ("X-rays"), computed tomography ("CT") scans, magnetic resonance images ("MRIs"), sonograms, mamograms, nuclear medicine studies and the like, are a vital tool in diagnosis, treatment planning and other aspects of healthcare delivery. One of the more recent advances in medical imaging was the ability to acquire digital images or to scan and digitize images which were originally acquired on radiographic or other non-digital film. Another advance enabled physicians and other healthcare workers to distribute those digital images over a network. One technology which has enhanced the transfer of radiologic images and other medical information between computers is DICOM (Digital Imaging and Communications in Medicine), which is the industry standard for transferring such images and information. Digitization often allows radiologists and other physicians and healthcare workers to more easily manipulate a given image for easier viewing. Distribution over a network allows those healthcare workers to view images from remote locations, such as a another hospital, an office or even a home.

One system and method for uploading medical images to a server or secure server for distribution over a network is provided by, for example, U.S. application Ser. No. 09/219,956, filed Dec. 23, 1998, which is hereby incorporated by reference. Using that system, currently marketed under the trade name Remote Image™, a hospital, urgent care facility or other healthcare provider may upload images to a secure server and distribute the images over a network. While Remote Image™ has improved the way medical images are viewed and evaluated, some problems with remote viewing still exist.

For example, physicians in many different specialties, especially surgeons, often implant devices into patients to repair the effects of trauma, disease, deterioration and the like. Since each patient has a unique anatomy, device manufacturers offer various styles, shapes and sizes of devices for any given surgical procedure. As device technology has advanced, manufacturers have greatly increased the variety and number of different devices available. This variety has often caused hospitals and other surgical facilities to keep very large inventories of devices on hand to ensure that the optimal device for each patient will be available. To address the problem of unwieldy inventories, device manufacturers and surgeons typically began utilizing pre-operative planning, wherein manufacturers provide "templates" of the available devices. Templates, in one embodiment, are images of devices which can be placed over patient images (such as X-rays) in order to determine the appropriate type, size and placement of a device prior to surgery. A template is typically an outline of a device, printed on clear film.

One issue that should be considered when using such templates is magnification. An X-ray of a bone, for example, often becomes magnified as a result of the distance between the bone and the X-ray cassette (which holds the film). This magnification is generally between 5% and 25%, depending upon the technique used and the anatomy of the patient. Thus, to help surgeons develop more accurate pre-operative plans, device manufacturers typically offer templates in multiple magnifications, such as 105%, 110%, 115% and 120%, to compensate for the X-ray magnification.

For proper pre-operative planning, a surgeon typically obtains multiple images of the affected anatomical area, such as a broken bone, from multiple views, such as frontal, side and oblique views. The surgeon may then compare multiple templates by placing each one in succession over the images of the broken bone. This pre-operative planning process helps surgeons determine the optimal type, size and placement of a device before operating. The process also reduces device inventory that a hospital or other surgical facility often keeps on hand. However, a surgical facility often acquires templates with several magnifications for each size and style of device from each device manufacturer. Although managing and storing an inventory of templates is preferable to managing and storing an inventory of devices, a large inventory of templates can become unwieldy as well. The orthopedic device industry alone, for example, includes hundreds of different manufacturers with several thousand different device systems currently on the market. The total number of parts included in all these orthopedic device systems thus easily numbers in the hundreds of thousands. These include hip joints, knee joints, shoulder joints, ankle joints, elbow joints, finger and toe joints, spinal implants, rods, plates, screws, pins, and countless other parts.

Thus, a need exists for systems and methods to enable surgeons and other healthcare providers to more efficiently view and evaluate images to conduct pre-operative planning A need also exists for systems and methods to enable healthcare providers to accomplish pre-operative planning from locations remote from a particular hospital. A need also exists for systems and methods to reduce the inventories of medical devices and medical device templates that hospitals and other surgical facilities typically keep on hand for operative procedures and pre-operative planning.

SUMMARY OF THE INVENTION

The present invention provides systems and methods for enhancing the viewing of medical images accessible via a secure server and a network. In one embodiment, a method includes acquiring and digitizing medical images, transmitting the medical images to an uploader device, transmitting the medical images to a secure server via a network, assembling a web page, including the medical images, transmitting the web page to an authorized user, and displaying a template on the web page, wherein said template comprises an image which the authorized user may place one or more of the medical images.

Other embodiments of the present invention include similar features but may enable an authorized user to view or manipulate medical images in other advantageous ways. For example, in one embodiment, a user may be provided with a goniometer function to measure one or more angles on a medical image. In another embodiment, two authorized users may be enabled to view the same image simultaneously and to send and receive messages to one another. In yet another embodiment, one or more authorized users may access a database of information, such as general medical information and patient information, while viewing a medical image.

BRIEF DESCRIPTION OF EXEMPLARY DRAWINGS

Additional aspects of the present invention will become evident upon reviewing the non-limiting embodiments described in the specification and the claims, in conjunction with the accompanying figures, wherein like numerals designate like elements:

DETAILED DESCRIPTION OF EXEMPLARY EMBODIMENTS

The following description is of exemplary embodiments only and is not intended to limit the scope, applicability or configuration of the invention in any way. Rather, the following description merely provides a convenient illustration for implementing exemplary embodiments of the invention. For example, various changes may be made in the design and arrangement of the elements described in the preferred embodiments without departing form the scope of the invention as set forth in the appended claims.

The present invention may be described herein in terms of functional block components and processing steps. It should be appreciated that such functional blocks may be realized by any number of hardware components configured to perform the specified functions. For example, the present invention may be implemented by various integrated circuit components, e.g., memory elements, logic elements, lookup tables, and the like, which may be used to carry out a variety of functions under the control of one or more microprocessors or other control devices. In addition, those skilled in the art will appreciate that the present invention may be realized in a software or computer program context in conjunction with any number of conventional computer system environments. Furthermore, the present invention is not limited to the process flows described herein, as any process flow or rearrangement of process steps which captures the features of the present invention is considered to be within the scope of the present invention. It should be noted that the present invention may employ any number of conventional techniques for processing steps such as a binary search, and the like. Such general techniques that may be known to those skilled in the art are not described in detail herein.

It should be appreciated that the particular implementations and processes shown and described herein are illustrative of the present invention and its best mode and are not intended to otherwise limit the scope of the present invention in any way. Indeed, for the sake of brevity, conventional object-oriented programming and other software programming techniques may not be described in detail herein.

Although exemplary embodiments are described in detail below in terms of systems and methods for providing and displaying medical images, it should be understood that the systems and methods of the present invention may be used to enhance the viewing of various other images over a network or without a network. For example, the present invention may enhance the viewing, manipulation and discussion of images by graphic designers, artists, businesses, and the like. Thus, the systems and methods of the present invention are not limited to medical or health-related uses or images.

According to one exemplary embodiment, the present invention relates to systems and methods to facilitate the viewing of images distributed over a network. In accordance with several aspects of exemplary embodiments of the present invention, improvements and enhancements are provided to the systems and methods described in U.S. patent application Ser. No. 09/219,956 ("the '956 application") filed Dec. 23, 1998 which is hereby incorporated by reference in its entirety. The systems and methods described in the '956 application comprise a secure network site, typically a secure site on the world wide web, for storing images and other data that have been uploaded by one or more medical service providers, such hospitals, urgent care facilities, radiological facilities and the like. To access a secure web site, a user (sometimes referred to herein as a "medical professional") may be required to provide a unique identifier, associated with the user, that is registered with the system. When a user's identifier has been authenticated, the user may view certain images stored in the system.

In accordance with one aspect of the present invention, images may be transferred between multiple uploading sites, multiple secure web sites and/or multiple users via any suitable transfer protocol and compression format. In one exemplary embodiment of the invention, DICOM 3.0 (Digital Imaging and Communications in Medicine) may be used. DICOM 3.0 is the industry standard for the transmission of radiologic images and other medical information between computers. Patterned after the Open System Interconnection of the International Standards Organization, DICOM 3.0 enables digital communication between diagnostic and therapeutic equipment and systems from various manufacturers. For example, workstations, CT scanners, MR imagers, film digitizers, shared archives, laser printers, and host computers and mainframes made by multiple vendors and located at one site or many sites can communicate by means of DICOM 3.0 across a network. Demonstration software for DICOM 3.0 is in the public domain and is available from the Mallinkrodt Institute of Radiology ftp server at ftp://ftp.ert.wustl.edu/pub/dicom, the entire contents of which is hereby incorporated by reference.

In one embodiment of the present invention, systems and methods for improved viewing of remote medical images are provided. For example, and with reference to FIG. 1, one embodiment of the present invention provides medical images for display on a viewing screen 100. In one embodiment, viewing screen 100 may include a management console 102 and a module window 202. Generally, management console 102 may be configured to function as a control panel, allowing a user to select images to be viewed, read information about images, control one or more aspects of images to be viewed and the like. Module window 202 may generally be configured to enable a user to view one or more images, view and input text, and/or make adjustments, modifications, measurements, additions and the like to images and/or text. Various embodiments of management console 102 and module window 202 are described in greater detail below. It should be understood that viewing screen 100 may include additional elements, such as multiple management consoles 102, multiple module windows 202 and/or any other suitable elements for enhancing the accessing, displaying, viewing, and/or modifying of medical images which are currently known or hereafter discovered by those skilled in the art.

Figure 1:
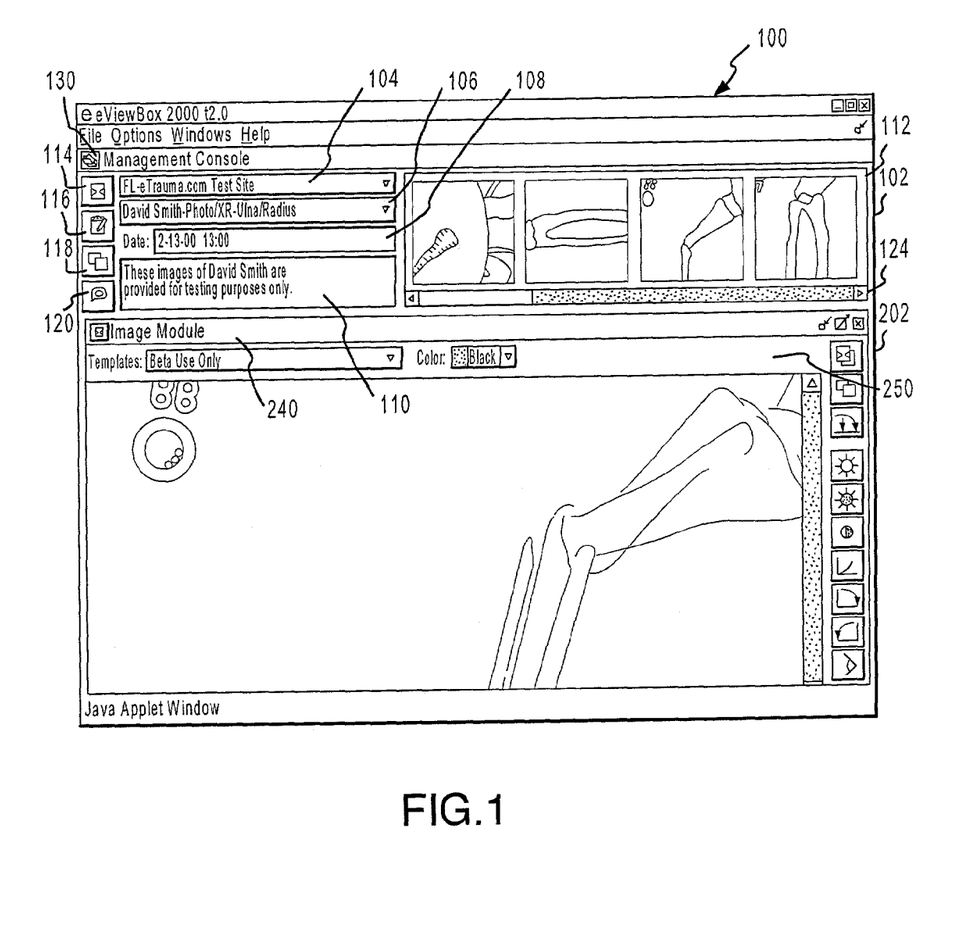
FIG. 1 is an exemplary screenshot demonstrating certain aspects of one embodiment of the invention, including a management console.

In one exemplary embodiment of the invention, management console 102 may include one or more menus (104, 106), one or more buttons (114, 116, 118, 120), one or more information windows (108, 110) and an image selection window 112. For example, in one embodiment, management console includes an upload site menu 104 and image menu 106, which may be configured to enable a user to select particular aspects of images for viewing. As shown in FIG. 1, upload site menu 104 and image menu 106 may be in the form of drop down menus. Upload site menu 104 may allow a user to select an upload site (e.g., a particular hospital, clinic or the like), from a drop-down list of multiple upload sites, from which the user wishes to view one or more images. Image menu 106 may allow a user to select one or more images, or sets of images, from the selected upload site, display on viewing screen 100. For example, in one embodiment, image menu 106 may be configured to provide a user with a list of patients. By selecting a patient from image menu 106, a user may view a set of images associated with that patient.

According to one aspect of the invention, users may be required to enter unique identifiers, such as passwords, to gain access to viewing screen 100. Identifiers may be used to determine whether particular users may have access to viewing screen 100. According to another aspect of the invention, identifiers may be used to determine a list of upload sites and/or a list of images which particular users may access. For example, one particular physician may be authorized to access images uploaded from hospital A only, while another physician may be authorized to access images uploaded from hospitals A and B. Yet another physician may be authorized to access images from hospitals A and B, but may only be authorized to access to images of orthopedic patients at those two hospitals. Thus, users who successfully access viewing screen 100 may be limited in their choices of upload sites from upload site menu 104 and/or in their choices of patients or images from image menu 106.

To achieve the authentication function described above, one exemplary system for providing and displaying medical images may includes a unique identifier storage and processor module. Such aspects of a system for providing and displaying medical images over a network are described in full in the '956 application, incorporated by reference above, and therefore will not be described in detail herein.

According to another aspect of the present invention, management console 102 may include one or more information windows, each of which may provide information to a user. For example, in one embodiment, management console 102 may include a date window 108 and an image description window 110. Date window 108 may provide the date and/or time at which a particular image was taken, the present date and time, the date and time a particular patient was admitted to a hospital and the like. Image description window 110 may provide a description of a particular image or set of images. For example, in FIG. 1, image description window 110 contains a description reading, "These images of David Smith are provided for testing purposes only." Text in the image description window may further include such patient information as date of admission to a healthcare facility, diagnosis, medications, treatment plan, planned discharge date and the like. Image description window 110 may also contain non-patient information or, in fact, any suitable information related to an image, set of images or the like.

In accordance with another aspect of the invention, management console 102 may further include an image selection window 112. Image selection window 112 may display one or more reduced-size images which may be selected for viewing in a larger format. For example, image selection window 112 may display a particular number of images that have been taken of a patient selected by a user from image menu 106. In FIG. 1, four images from a patient are displayed in image selection window 112. In one embodiment, image selection window 112 may also include a scrollbar 124 or similar device for moving through images within the window. Image selection window 112 may be configured to allow a user to select one of the displayed images for viewing in a larger format in module window 202. In one embodiment, selection may be accomplished by dragging an icon onto an image and selecting the image, for example with a mouse on a computer. In another embodiment, image selection window 112 may be configured as a touch sensitive screen, so that a user may select an image by touching the image on the screen. Image selection window 112 may include any suitable configuration of displayed images and any means for selecting one of the displayed images which are now known or may be discovered in the future.

According to another aspect of the invention, management console 102 may further include one or more module selection buttons (114, 116, 118, 120), for selecting one or more modules to be displayed in module window 202. For example, in one embodiment, management console 102 may include an image module selector button 114, a documentation module selector button 116, a templating module selector button 118 and a discussion module selector button 120. Clicking on, or otherwise selecting, one or more of these module selector buttons allows a user to view one or more modules on module window 202. Various aspects of various modules will be described in further detail below. According to one aspect of the present invention, management console 102 and various modules may be provided via Java applets.

Figure 2:
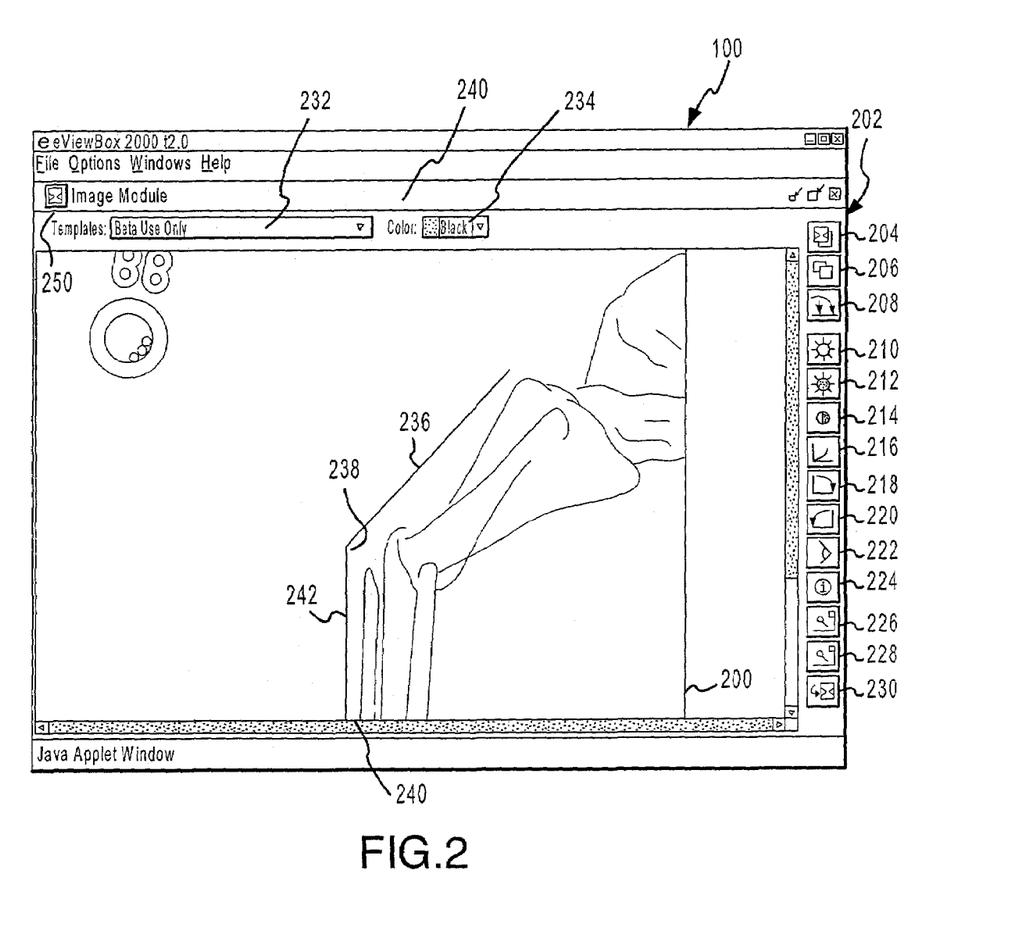
FIG. 2 is an exemplary screenshot demonstrating certain aspects of another embodiment of the invention, including an image module.
Figure 3:
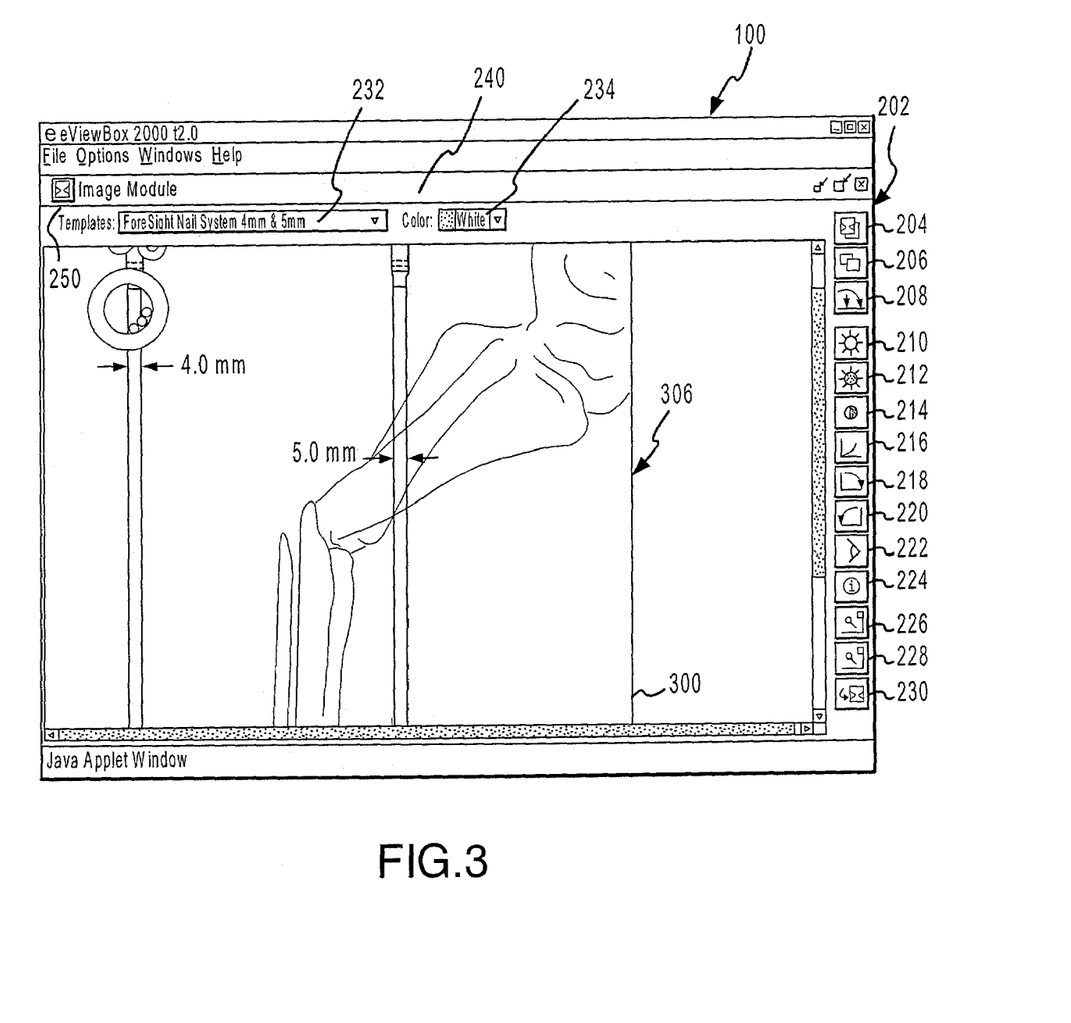
FIG. 3 is an exemplary screenshot demonstrating certain aspects of another embodiment of the invention, including a templating module.
Figure 4:
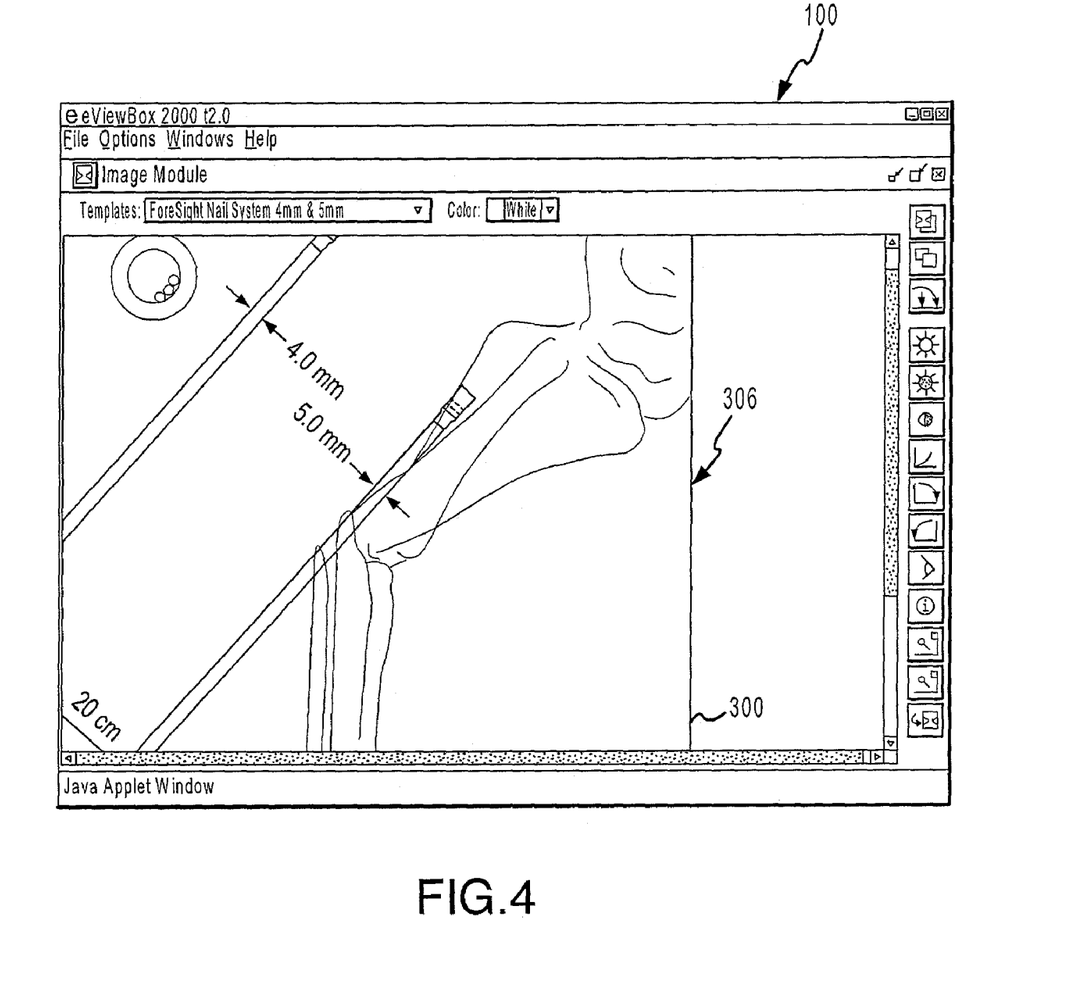
FIG. 4 is an exemplary screenshot demonstrating certain aspects of another embodiment of the invention, including a templating module as shown in FIG. 3, with image manipulations having been executed on the selected template.

In accordance with another aspect of the present invention, as shown in FIG. 1, management console 102 and module window 202 may be viewed simultaneously on viewing screen 100. Alternatively, management console 102 may be closed, for example by clicking on a management console button 130. FIGS. 2, 3 and 4 show viewing screen with management console 102 closed and with module window 202 displayed on viewing screen 100.

In one embodiment of the invention, module window 202 may display one or more various modules. For example, in FIGS. 1–4, module window 202 includes an image module 240 and a templating module 250. As shown in FIG. 1, a user may select one or more modules to be displayed on module window by clicking on, or otherwise selecting, one or more module selection buttons 114, 116, 118 and 120 on management console 102. When image module 240 has been selected via image module selection button 114, an image 200 may be chosen for viewing within image module 240. This may be accomplished, for example, by user selecting image 200 from image selection window 112.

In one embodiment of the present invention, image module 240 may be configured to display selected images and enable a user to manipulate particular features of the images. In one embodiment, image module 240 may include one or more buttons to allow manipulation of image 200 and/or other various features of image module 240, described in greater detail below. Examples of buttons on image module 240 may include, but are not limited to, a brightness button 210, a darkness button 212, a contrast button 214, a clockwise rotation button 218, a counterclockwise rotation button 220, a size magnification button 226 and a size reduction button 228. Other buttons may include an image reset button 230, configured to reset the characteristics of image 200 to those it originally had before manipulation by a user. According to another aspect of the invention, additional buttons may include, but are not limited to a rotation button 208, configured to allow a user to rotate image 200 about a user-defined axis and a gamma correction button 216, configured to enable a user to set the gamma correction for image 200.

In viewing and analyzing radiographs ("X-rays"), CT scans, MRI scans and the like, a medical professional or other user often measures one or more angles between particular bones, bone parts or other anatomical or device features. Typically, a medical professional may measure such angles on a film by holding a goniometer (a device for measuring solid angles) up to a film. As described above in the Background section, however, that traditional technique for measuring angles has inherent drawbacks, in that films may magnify or otherwise distort normal anatomy and holding a goniometer in front of a viewing screen is generally awkward.

In one embodiment of the present invention, a system and method is provided for enabling a medical professional or other user to more easily make angular measurements on films. Such measurements may be provided on image module 240 via a goniometer button 222. In one embodiment, a user may select goniometer button 222 by clicking on the that button 222. The user may then click on two locations within image 200 to draw (or "place") a first line 236 or vector of the angle to be measured, with the second location defining the vertex 238 of the angle. The user may then click on a third location to place a second line 242 or vector of the angle to be measured, the second line running from the vertex 238 of the angle to the third location clicked by the user. Image module 240 then measures and displays 244 the angle created between the two lines 236 and 242 created by the user and updates the angle if any changes are made in the location of the either of the two lines 236 and 242. For example, a user may place the third location in one spot on image 200 and then move it to various other locations until the user believes the line is most accurate. According to one aspect of the invention, display 244 of the angle may be constantly updated as the location of one or both lines 236 and 242 change. In one embodiment of the invention, if a user wishes to view the bit size of the image, the user may click on or otherwise select a bit size button 224 and display 244 will then show bit size, rather than the measured angle.

In one embodiment of the invention, as shown in FIGS. 1–4, module window 202 may contain image module 240 as well as a templating module 250. In the embodiment shown in FIG. 2, templating module 250 consists of two drop-down menus 232 and 234 displayed within image module 240. FIG. 3 is a screen shot, displaying an exemplary embodiment of templating module 250 in which a user has made selections from drop-down menus 232 and 234. In that embodiment, templating module 250 is configured to enhance image module 240 by allowing a user to view image 200 in image module 240 and to also select device templates and device template characteristics to place and view the templates on image 200. For example, templating module 250 may include a template selection menu 232 and a template color selection menu 234. Template selection menu 232 may contain a drop-down list of templates from which a user may select a template for viewing. In FIG. 3, a user has selected "ForeSight Nail System 4 mm & 5 mm" as a device template to view. The user has also chosen white as the color for the template from template color selection menu 234. A template 306 appears as an overlay (analogous to a transparency which might be placed over a conventional film), including two white-line images of devices superimposed on image 200 originally selected for viewing by the user.

Image 200 is an X-ray of a broken ulna bone, one of the bones of the forearm. The device chosen by a user as template 306 is a type of bone pin. Template 306 shows two different sizes of the particular brand and model bone pin chosen, having diameters of 4 mm and 5 mm. Using one template to show multiple sizes of a device allows a user to more easily compare the fit of those multiple sizes of the device onto the part of a patient to be treated. In one embodiment, different colors can be chosen from template color selection menu 234 for different sizes of devices, further enabling a user to distinguish between and compare two or more sizes of a device.

According to yet another aspect of the present invention, image module 240 and templating module 250 may include an image adjustment button 204 and a template adjustment button 206. A user may select image adjustment button 204 to make adjustments or manipulations to image 200 or may select template adjustment button 206 to make adjustments or manipulations to template. When one of adjustment buttons 204 and 206 is selected, that feature may be adjusted and the other feature remains fixed.

As shown in FIG. 4, template 306 can be rotated with respect to image 200, and vice versa. To do so, a user may first choose an axis of rotation by clicking on rotation button 208 and then clicking on a desired point on image 200 (which will then be the axis). The user may then select, or "grab" template 306, for example by grabbing with an icon controlled by a mouse, and may rotate template 306 about the axis selected by the user. In one embodiment, when template adjustment button 206 has been selected, contrast button 214 or gamma correction button 216 can used to adjust those characteristics of template 306. Additionally, goniometer button 222 may be used to measure one or more angles between template 306 and image 200, in the same way that goniometer button 222 was described above.

According to another aspect of the invention, template 306 can easily be modified to reflect any desired image magnification, not just the standard 5%, 10%, 15% and 20% magnifications available using conventional templates. To determine the magnification of a particular image, a healthcare professional may place a radiopaque gauge near to the patient being imaged, so that the gauge will be clearly visible on the image and a user viewing the image can use the gauge to measure the magnification of the image. Template 306 can then be chosen based on that magnification measurement.

Figure 5:
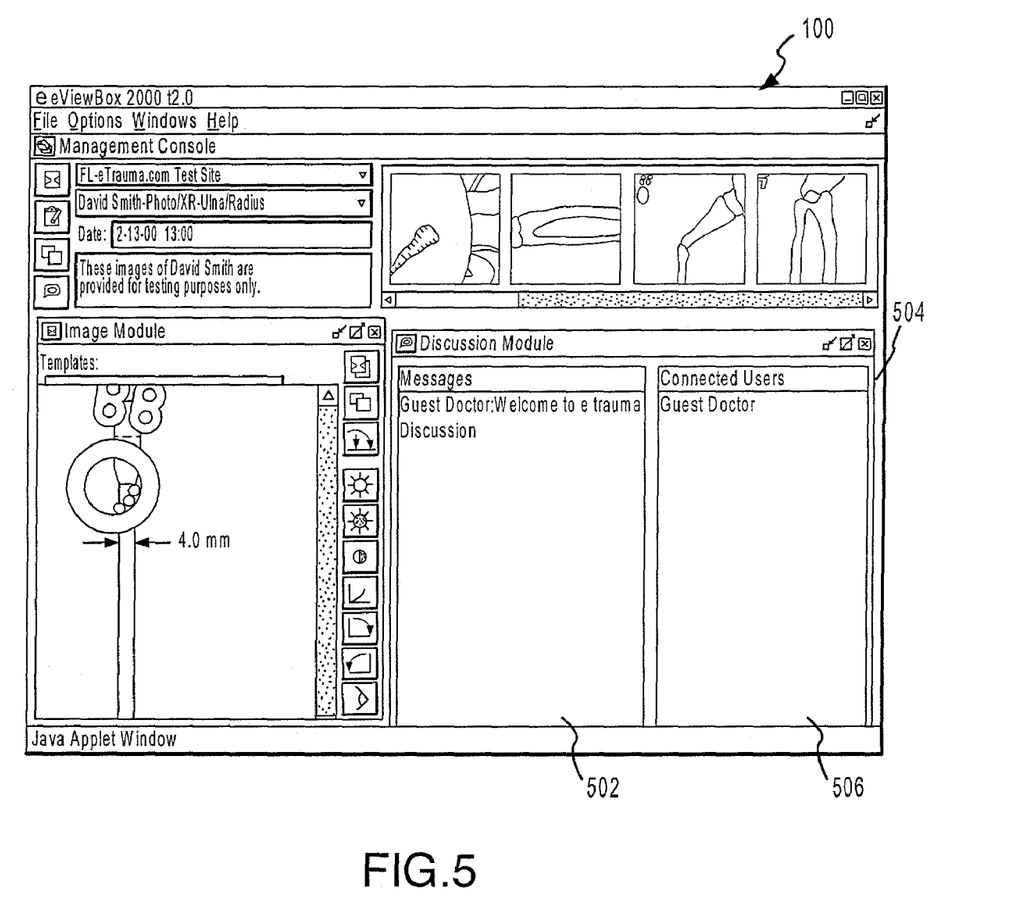
FIG. 5 is an exemplary screenshot demonstrating certain aspects of another embodiment of the invention, including a discussion module.

FIG. 5 is a screen shot showing certain aspects of one embodiment of the present invention, including a discussion module 504. Discussion module 504 may be displayed together with image module 240, template module 250 and/or other modules, in module window 202. In one embodiment, discussion module 504 includes a message window 502 and a user list window 506. Message window 502 is configured to display messages input by one or more users who are viewing or have viewed images in image module 240. User list window 506 displays the names, passwords or other identifying indicia of users accessing and viewing images in image module 240.

Discussion module 504 may be accessed and used, for example, by medical professionals, device manufacturers and/or other authorized users and may enhance diagnosis, pre-operative planning, post-operative review and other aspects of healthcare services, research and the like. According to one embodiment of the present invention, two or more users may access and view the same image or set of images simultaneously in image module 240 and those users may input and read messages amongst themselves via discussion module 504. Additionally, according to another aspect of the invention, these users may view and discuss images while one or more users are manipulating the image and/or a template. When a discussion via discussion module 504 is completed, the discussion may be saved in association with the image or set of images being discussed, and all such discussions may be archived for subsequent review. According to yet another aspect of the invention, discussion module 504 may also support the transfer of real-time audio between two or more users.

According to yet another aspect of the present invention, systems and methods may be provided to enable a user to email a link associated with the image or images, an actual image itself, or the like to another user. In one embodiment, images may only be emailed to one of the persons authorized to view the particular image. In a further alternate embodiment, voice recognition and/or text-to-speech capabilities are supported.

A further aspect of the invention according to one embodiment is a documentation module. Documentation module (not shown) may be selected by one or more users by selecting documentation module button 116. When documentation module is selected, user may choose from one or more drop-down menus to view documentation associated with a particular patient, image or set of images selected by the user from management console 102 for viewing on viewing screen 100. Examples of documentation may include, but is not limited to, patient medical records, insurance information, or information provided by one or more radiologists and the like. Furthermore, in accordance with one aspect, documentation may be stored and displayed in image format, text format, or both.

In accordance with yet another aspect of the invention, a database of information may be provided. Such information may include, for example, messages between two or more users recorded from discussion module 504, general information regarding medical conditions or radiological conditions, patient information and histories and the like. For example, a database of orthopedic devices sold by one or more device manufacturers may be provided, including data on indications for use of a given device and instructions for use of the device. More general medical information may also be stored and accessed and may, in fact, be illustrated using images shown through the image module. Such a database of information may be accessible via a button, located anywhere on viewing screen 100.

Information stored by a medical professional, medical device company, hospital or any other entity involved in the system and method described by the present invention may be stored in a computerized database. Database may be any type of database, such as relational, hierarchical, object-oriented, and/or the like. Common database products that may be used to implement database include DB2 by IBM (White Plains, N.Y.), any of the database products available from Oracle Corporation (Redwood Shores, Calif.), Microsoft Access by Microsoft Corporation (Redmond, Wash.), or any other database product. Database may be organized in any suitable manner, including as data tables or lookup tables. Association of certain data may be accomplished through any data association technique known and practiced in the art. For example, the association may be accomplished either manually or automatically. Automatic association techniques may include, for example, a database search, a database merge, GREP, AGREP, SQL, and/or the like. The association step may be accomplished by a database merge function, for example, using a "key field" in each of the manufacturer and retailer data tables. A "key field" partitions the database according to the high-level class of objects defined by the key field. For example, a certain class may be designated as a key field in both the first data table and the second data table, and the two data tables may then be merged on the basis of the class data in the key field. In this embodiment, the data corresponding to the key field in each of the merged data tables is preferably the same. However, data tables having similar, though not identical, data in the key fields may also be merged by using AGREP, for example.

The system according to the present invention may include a host server or other computing systems including a processor for processing digital data, a memory coupled to said processor for storing digital data, an input digitizer coupled to the processor for inputting digital data, an application program stored in said memory and accessible by said processor for directing processing of digital data by said processor, a display coupled to the processor and memory for displaying information derived from digital data processed by said processor and a plurality of databases, said databases including patient data, medical device data, radiological data and the like, as described above. As those skilled in the art will appreciate, a computer used by a medical professional to access and use this system may include an operating system (e.g., Windows 95/97/98/2000, Linux, Solaris, etc.) as well as various conventional support software and drivers typically associated with computers. The user's computer can be in a home or business environment with access to a network. In an exemplary embodiment, access is through the Internet through a commercially-available web-browser software package.

The user's computer may provide a suitable web site or other Internet-based graphical user interface which is accessible by users. In one embodiment, the Internet Information Server, Microsoft Transaction Server, and Microsoft SQL Server, are used in conjunction with the Microsoft operating system, Microsoft NT web server software, a Microsoft SQL database system, and a Microsoft Commerce Server. Additionally, components such as Access Sequel Server, Oracle, Mysequel, Intervase, etc., may be used to provide an ADO-compliant database management system. The term "web page" as it is used herein is not meant to limit the type of documents and applications that might be used to interact with the user. For example, a typical web site might include, in addition to standard HTML documents, various forms, Java applets, Javascript, active server pages (ASP), common gateway interface scripts (CGI), extensible markup language (XML), dynamic HTML, cascading style sheets (CSS), helper applications, plug-ins, and the like.

The present invention may be described herein in terms of functional block components, screen shots, optional selections and various processing steps. It should be appreciated that such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, the software elements of the present invention may be implemented with any programming or scripting language such as C, C++, Java, COBOL, assembler, PERL, extensible Markup Language (XML), with the various algorithms being implemented with any combination of data structures, objects, processes, routines or other programming elements. Further, it should be noted that the present invention may employ any number of conventional techniques for data transmission, signaling, data processing, network control, and the like. Still further, the invention could be used to detect or prevent security issues with a client-side scripting language, such as JavaScript, VBScript or the like. For a basic introduction of cryptography, please review a text written by Bruce Schneider which is entitled "Applied Cryptography: Protocols, Algorithms, And Source Code In C," published by John Wiley & Sons (second edition, 1996), which is hereby incorporated by reference.

It will be appreciated that many applications of the present invention could be formulated. One skilled in the art will appreciate that the network may include any system for exchanging data or transacting business, such as the Internet, an intranet, an extranet, WAN, LAN, satellite communications, and/or the like. It is noted that the network may be implemented as other types of networks, such as an interactive television (ITV) network. The users may interact with the system via any input device such as a keyboard, mouse, kiosk, personal digital assistant, handheld computer (e.g., Palm Pilot®), cellular phone and/or the like. Similarly, the invention could be used in conjunction with any type of personal computer, network computer, workstation, minicomputer, mainframe, or the like running any operating system such as any version of Windows, Windows NT, Windows2000, Windows 98, Windows 95, MacOS, OS/2, BeOS, Linux, UNIX, Solaris or the like. Moreover, the invention may be implemented with TCP/IP communications protocols, IPX, Appletalk, IP-6, NetBIOS, OSI or any number of existing or future protocols. Moreover, the system contemplates the use, sale or distribution of any goods, services or information over any network having similar functionality described herein.

Any computing units utilized by the system according to one embodiment of the present invention may be connected with each other via a data communication network. The network may be a public network and assumed to be insecure and open to eavesdroppers. In the illustrated implementation, the network may be embodied as the Internet. In this context, the computers may or may not be connected to the Internet at all times. For instance, a medical professional's computer may employ a modem to occasionally connect to the Internet, whereas a hospital's computer system might maintain a permanent connection to the Internet. Specific information related to the protocols, standards, and application software utilized in connection with the Internet may not be discussed herein. For further information regarding such details, see, for example, DILIP NAIK, INTENET STANDARDS AND PROTOCOLS (1998); JAVA 2 COMPLETE, various authors, (Sybex 1999); DEBORAH RAY AND ERIC RAY, MASTERING HTML 4.0 (1997). LOSHIN, TCP/IP CLEARLY EXPLAINED (1997). All of these texts are hereby incorporated by reference.

The systems may be suitably coupled to network via data links. A variety of conventional communications media and protocols may be used for data links, such as a connection to an Internet Service Provider (ISP) over the local loop as is typically used in connection with standard modem communication, cable modem, Dish networks, ISDN, Digital Subscriber Line (DSL), or various wireless communication methods. A healthcare provider's computer system might also reside within a local area network (LAN) which interfaces to network via a leased line (T1, D3, etc.). Such communication methods are well known in the art, and are covered in a variety of standard texts. See, e.g., GILBERT HELD, UNDERSTANDING DATA COMMUNICATIONS (1996), hereby incorporated by reference.

As will be appreciated by one of ordinary skill in the art, the present invention may be embodied as a method, a data processing system, a device for data processing, and/or a computer program product. Accordingly, the present invention may take the form of an entirely software embodiment, an entirely hardware embodiment, or an embodiment combining aspects of both software and hardware. Furthermore, the present invention may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

Communication between one or more users and the system according to the present invention may be accomplished through any suitable communication means, such as, for example, a telephone network, Intranet, Internet, point of interaction device (point of sale device, personal digital assistant, cellular phone, kiosk, etc.), online communications, offline communications, wireless communications, and/or the like. One skilled in the art will also appreciate that, for security reasons, any databases, systems, or components of the present invention may consist of any combination of databases or components at a single location or at multiple locations, wherein each database or system includes any of various suitable security features, such as firewalls, access codes, encryption, de-encryption, compression, decompression, and/or the like.

In the foregoing specification, the invention has been described with reference to specific embodiments. However, it will be appreciated that various modifications and changes can be made without departing from the scope of the present invention as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical".

We claim:

1. A method for facilitating the transmission and display of a medical image, via a server and a network, the method comprising:
   acquiring and digitizing said medical image using an acquiring device;
   transmitting said medical image to said server via said network;
   assembling a web page, including said medical image, at said sewer;
   transmitting said web page to an authorized user, wherein said authorized user inputs a unique identifier;
   displaying a template on said web page, wherein said template comprises an image which said authorized user incorporates into said medical image; and,
   facilitating real time interaction by a plurality of authorized users to place and manipulate at least one of said template and said medical image, wherein interaction by a first authorized user with at least one of said template and said medical image is viewable by said plurality of authorized users in real time.

2. The method of claim 1, further comprising:
   providing a list of templates; and
   allowing said authorized user to select said templates from said list of templates.

3. The method of claim 2, wherein said list of templates includes at least two different sizes of a same medical device.

4. The method of claim 1, wherein said template includes at least one image of a medical device.

5. The method of claim 1, further comprising enabling said authorized user to move said template to a plurality of locations on a viewing device.

6. The method of claim 1, further comprising enabling said authorized user to move said said medical image to a plurality of locations on a viewing device.

7. The method of claim 1, further comprising allowing said authorized user to choose whether said template includes at least one of a black and white color.

8. The method of claim 1, further comprising allowing said authorized user to adjust the gamma correction for said medical image.

9. The method of claim 1, further comprising enabling said authorized user to manipulate display characteristics of said said medical image.

10. The method of claim 9, wherein said display characteristics include at least one of contrast, gamma settings, image magnification, image size reduction and image rotation.

11. The method of claim 1, further comprising allowing said authorized user to access a database of information while viewing said medical image.

12. The method of claim 11, wherein said information includes general medical information and patient information.

13. The method of claim 1, further comprising facilitating real time interaction by a plurality of authorized users to place and manipulate at least one of said template and said medical image, wherein interaction by said plurality of authorized users with at least one of said template and said medical image is viewable by said plurality of authorized users in real time.

14. A method for facilitating the transmission and display of a medical image, via a server and a network, the method comprising:
   acquiring and digitizing said medical image using an acquiring device;
   transmitting said medical image to said server via said network;
   assembling a web page, including said medical image, at said server;
   transmitting said web page to an authorized user, wherein said authorized user inputs a unique identifier;
   allowing said authorized user to place two connected lines on said medical image;
   measuring an angle formed by the junction of said two connected lines; and
   displaying said measurement of said angle to said authorized user;
   displaying a template on said web page according to said measurement, wherein said template comprises an image which said authorized user incorporates into said medical image; and,
   facilitating real time interaction by a plurality of authorized users to place and manipulate said template and said medical image, wherein said interaction by said first authorized user with at least one of said template and said medical image is viewable by a plurality of authorized users in real time.

15. A method for facilitating the transmission and display of a medical image, via a server and a network, the method comprising:
   acquiring and digitizing said medical image using an acquiring device;
   transmitting said medical image to said server via said network;
   assembling a web page, including said medical image, at said server;
   transmitting said web page to a first authorized user, wherein said first authorized user inputs a first unique identifier;
   transmitting said web page to a second authorized user, wherein said second authorized user inputs a second unique identifier;
   displaying a message area;
   accepting messages input by said at least one of said first authorized user and said second authorized user;
   displaying said messages in said message area; and,
   facilitating interaction by at least one at said first authorized user and said second authorized user to place and manipulate a template and said medical image, wherein said interaction by said first authorized user with at least one of said template and said medical image is viewable by said second authorized user in real time.

16. The method of claim 15, further comprising displaying a list including the names of said first and second authorized users.

17. The method of claim 15, further comprising storing said messages on said server.

18. A method for facilitating the transmission and display of a medical image for viewing, via a server and a network, the method comprising:

receiving said medical image on said server from at least one uploading locations;

storing said medical image on said server;

accepting a log-on request from a user to log onto said server, wherein said log-on request includes inputting a unique identifier;

accepting a viewing request from said user to view said medical image;

determining, based on said unique identifier and said viewing request, whether said user is authorized to view said at least one of said medical image;

displaying said medical image to said authorized user, based on said determining step and said viewing request;

facilitating real time interaction by a plurality of authorized users to place and manipulate a template and said medical image;

allowing said plurality of authorized users to place said template on said medical image;

allowing said plurality of authorized users to move said template to another location on said medical image;

accepting a message from said authorized user;

displaying said message; and displaying said medical image, said template and said message to said plurality of authorized users to facilitate interaction among said plurality of users to place and manipulate said template and said medical image, wherein interaction by a first authorized user with said template and said medical image is viewable by said plurality of authorized users in real time.

19. A system for facilitating the display of a medical image comprising:

a server for receiving said medical image from an uploading site;

a processor for processing requests of a plurality of users to log onto said server and view said medical image; p1 a database for storing a template, wherein said template is configured to be displayed with said medical image; and, for storing information associated with said template; and, a network for delivering said medical image, said template and said information to said plurality of users and to facilitate interaction by said plurality of users to place and manipulate said template and said medical image, wherein said interaction by a first authorized user with said template and said medical image is viewable by said plurality of authorized users in real time.

20. The system of claim 19, wherein said server is further configured to store said medical image.

21. The system of claim 19, wherein said processor comprises;

a storage module for storing unique user identifiers;

an comparison module for comparing said stored unique user identifiers with input unique user identifiers input by users; and an authorization module for analyzing results from said comparison module and at least one of authorizing and denying user log-on requests based on said results.

22. The system of claim 19, further comprising a second database for storing general medical information and patient information.

* * * * *